US00PP20193P2

(12) United States Plant Patent
Bergman

(10) Patent No.: US PP20,193 P2
(45) Date of Patent: Jul. 28, 2009

(54) ***CHRYSANTHEMUM* PLANT NAMED 'YOKINGSVILLE'**

(50) Latin Name: *Yokingsville*
Varietal Denomination: Chrysathemum×morifolium

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 12/214,216

(22) Filed: Jun. 16, 2008

(51) Int. Cl.
*A01H 5/00* (2006.01)

(52) U.S. Cl. ..... Plt./289
(58) Field of Classification Search ..... Plt./289
See application file for complete search history.

*Primary Examiner*—Annette H Para
(74) *Attorney, Agent, or Firm*—C. A. Whealy

(57) ABSTRACT

A new and distinct cultivar of *Chrysanthemum* plant named 'Yokingsville', characterized by its compact, upright, outwardly spreading and uniformly mounded plant habit; strong and vigorous growth habit; freely branching habit; dark green-colored foliage; uniform, freely and early flowering habit; decorative-type inflorescences with bright yellow-colored ray florets; and excellent postproduction longevity.

1 Drawing Sheet

Botanical designation: *Chrysanthemum×morifolium.*
Cultivar denomination: 'YOKINGSVILLE'.

BACKGROUND OF THE INVENTION

The present invention relates to a new and distinct cultivar of *Chrysanthemum* plant, botanically known as *Chrysanthemum×morifolium,* commercially grown as a pot-type *Chrysanthemum* and hereinafter referred to by the name 'Yokingsville'.

The new *Chrysanthemum* is a product of a breeding program conducted by the Inventor in Fort Myers, Fla. The objective of the breeding program is to create new pot-type *Chrysanthemum* cultivars that are suitable for year-round production with uniform plant growth habit, freely branching habit, good vigor, desirable inflorescence form and floret colors, fast response time and excellent postproduction longevity.

The new *Chrysanthemum* originated from a cross-pollination made by the Inventor in January, 2001, in Salinas, Calif. of a proprietary selection of *Chrysanthemum×morifolium* identified as code number YB-A0406, not patented, as the female, or seed, parent with a proprietary selection of *Chrysanthemum×morifolium* identified as code number YB-A0351, not patented, as the male, or pollen, parent. The new *Chrysanthemum* was discovered and selected by the Inventor as a single flowering plant within the progeny of the stated cross-pollination in a controlled greenhouse environment in Fort Myers, Fla. in March, 2002.

Asexual reproduction of the new *Chrysanthemum* by vegetative tip cuttings was first conducted in a controlled greenhouse environment in Fort Myers, Fla. in June, 2002. Asexual reproduction by cuttings has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yokingsville'. These characteristics in combination distinguish 'Yokingsville' as a new and distinct pot-type *Chrysanthemum* cultivar:

1. Compact, upright, outwardly spreading and uniformly mounded plant habit.
2. Strong and vigorous growth habit.
3. Freely branching habit.
4. Dark green-colored foliage.
5. Uniform, freely and early flowering habit.
6. Decorative-type inflorescences with bright yellow-colored ray florets.
7. Excellent postproduction longevity with inflorescences maintaining good substance and color for about five weeks in an interior environment.

Plants of the new *Chrysanthemum* differ from plants of the female parent selection in the following characteristics:

1. Plants of the new *Chrysanthemum* are more compact than plants of the female parent selection.
2. Plants of the new *Chrysanthemum* flower 1.5 weeks earlier than plants of the female parent selection.
3. Plants of the new *Chrysanthemum* and the female parent selection differ in ray floret color as plants of the female parent selection have yellow gold-colored ray florets.

Plants of the new *Chrysanthemum* differ from plants of the male parent selection in the following characteristics:

1. Plants of the new *Chrysanthemum* do not produce disc florets whereas plants of the male parent selection produce disc florets.
2. Plants of the new *Chrysanthemum* and the male parent selection differ in ray floret color as plants of the male parent selection have lighter yellow-colored ray florets.

Plants of the new *Chrysanthemum* can be compared to plants of *Chrysanthemum×morifolium* 'Yocovington', disclosed in U.S. Plant Pat. No. 13,031. In side-by-side comparisons conducted in Fort Myers, Fla., plants of the new *Chrysanthemum* primarily from plants of 'Yocovington' in the following characteristics:

1. Plants of the new *Chrysanthemum* flowered one to two days later than plants of 'Yocovington'.
2. Inflorescences of plants of the new *Chrysanthemum* maintained tight closed centers whereas inflorescences of plants of 'Yocovington' had open centers when grown under low light conditions.

BRIEF DESCRIPTION OF THE PHOTOGRAPH

The accompanying photograph illustrates the overall appearance of the new *Chrysanthemum*. This photograph shows the colors as true as it is reasonably possible to obtain in colored reproductions of this type. Colors in the photograph may differ slightly from the color values cited in the detailed botanical description which accurately describe the colors of the new *Chrysanthemum*. The photograph comprises a side perspective view of typical flowering plants of 'Yokingsville' grown in a container.

DETAILED BOTANICAL DESCRIPTION

The aforementioned photograph and following observations and measurements describe plants grown in Leamington, Ontario, Canada during the autumn in a glass-covered greenhouse and under conditions and practices which approximate those generally used in commercial pot-type *Chrysanthemum* production. During the production of the plants, day temperatures ranged from about 21° C. to 27° C. night temperatures ranged from about 17° C. to 19° C. and light levels ranged from 4,000 to 6,000 foot candles. Four unrooted cuttings were directly stuck in 15-containers, exposed to long day/short night conditions, and pinched about three weeks later. At the time of the pinch, the photoinductive short day/long night treatments were started. Plants used in the photograph and for the description were grown as natural sprays and were eleven weeks from planting. In the following description, color references are made to The Royal Horticultural Society Colour Chart, 1995 Edition, except where general terms of ordinary dictionary significance are used.

Botanical classification: *Chrysanthemum×morifolium* 'Yokingsville'.

Parentage:

*Female, or seed, parent.*—Proprietary selection of *Chrysanthemum×morifolium* identified as code number YB-A0406, not patented.

*Male, or pollen, parent.*—Proprietary selection of *Chrysanthemum ×morifolium* identified as code number YB-A0351, not patented.

Propagation:

*Type.*—Terminal vegetative cuttings.

*Time to initiate roots.*—About four days at temperatures of 21° C.

*Time to produce a rooted young plant.*—About ten days at temperatures of 21° C.

*Root description.*—Fine to thick, fibrous; white in color.

*Rooting habit.*—Freely branching; moderately dense.

Plant description:

*Appearance.*—Herbaceous decorative pot-type *Chrysanthemum* typically grown as a natural spray type. Compact; stems upright and outwardly spreading giving a uniformly mounded appearance to the plant. Freely branching habit, about four lateral branches develop after removal of terminal apex (pinching); dense and fill plant habit. Strong and vigorous growth habit.

*Plant height.*—About 28 cm.

*Plant width.*—About 45 cm.

*Lateral branches.*—Length: About 22 cm. Diameter: About 5 mm. Internode length: About 2.7 cm. Strength: Strong. Texture: Pubescent. Color: Close to 144A.

Foliage description:

*Arrangement.*—Alternate, simple.

*Length.*—About 6.5 cm.

*Width.*—About 4.5 cm.

*Shape.*—Palmately lobed.

*Apex.*—Cuspidate.

*Base.*—Truncate.

*Margin.*—Palmately lobed, sinuses between lateral lobes mostly parallel.

*Texture, upper and lower surfaces.*—Fine pubescence; veins prominent on lower surface.

*Color.*—Developing and fully expanded leaves, upper surface: Close to 147A; venation, close to 147A to 147B. Developing and filly expanded leaves, lower surface: Close to 147B; venation, close to 147B.

*Petiole.*—Length: About 1.9 cm. Diameter: About 3 mm. Texture, upper and lower surfaces: Pubescent. Color, upper surface: Close to 147B; towards the margin, close to 147A. Color, lower surface: Close to 147B to 147C; towards the margin, close to 147B.

Inflorescence description:

*Appearance.*—Decorative-type inflorescence form with elongated oblong-shaped ray florets. Inflorescences borne on terminals above foliage. Ray florets arranged acropetally on a capitulum. Inflorescence slightly fragrant; pleasant. Typically grown as a natural spray type.

*Flowering response.*—Under natural conditions, plants flower in the autumn/winter in the Northern Hemisphere. At other times of the year, inflorescence initiation and development can be induced under short day/long night conditions (at least 13.5 hours of darkness). Early flowering habit; plants exposed to three weeks of long day/short night conditions followed by photoinductive short day/long night conditions flower about 7.5 weeks later.

*Postproduction longevity.*—Inflorescences maintain good color and substance for about five weeks in an interior environment.

*Quantity of inflorescences.*—Freely flowering, about nine inflorescences develop per lateral stem.

*Inflorescence bud.*—Height: About 5 mm. Diameter: About 7.5 mm. Shape: Oblate. Color: Close to 141A.

*Inflorescence size.*—Diameter: About 8.6 cm. Depth (height): About 2 cm. Diameter of disc: No disc florets observed. Receptacle height: About 5 mm. Receptacle diameter: About 6 mm. Receptacle color: Close to 146B.

*Ray florets.*—Shape: Elongated oblong. Orientation: Initially upright, then with development, close to 90° from vertical. Aspect: Initially incurved, then mostly flat. Length: About 4.2 cm. Width: About 1 cm. Apex: Emarginate, acute or rounded. Base: Attenuate; short corolla tube. Margin: Entire. Texture, upper and lower surfaces: Smooth, glabrous; satiny. Number of ray florets per inflorescence: About 211 arranged in numerous whorls. Color: When opening, upper surface: Close to 6A to 6B. When opening, lower surface: Close to 6D. Fully expanded, upper surface: Close to 6B to 6C; with development, color becoming closer to 6C. Fully expanded, lower surface: Close to 6D.

*Disc florets.*—None observed.

*Phyllaries.*—Number of phyllaries per inflorescence: About 18 arranged in two to three whorls. Length: About 9 mm. Width: About 4 mm. Shape: Lanceolate. Apex: Acute. Base: Truncate. Margin: Entire. Texture, upper surface: Smooth, waxy. Texture, lower surface: Pubescent. Color, upper surface: Close to 141A. Color, lower surface: Darker than 141A.

*Peduncles.*—Length: First peduncle: About 2.2 cm. Fourth peduncle: About 3.4 cm. Seventh peduncle: About 4.1 cm. Diameter (first peduncle): About 2 mm. Angle: About 45° from vertical. Strength: Strong, flexible. Texture: Pubescent. Color: Close to 144A.

*Reproductive organs.*—Androecium: Not observed. Gynoecium: Pistil length: About 4 mm. Stigma shape: Bi-parted. Stigma color: Close to 9A. Style length: About 3 mm. Style color: Close to 145D.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* tolerate temperatures ranging from about 5° C. to about 38° C.

It is claimed:

1. A new and distinct *Chrysanthemum* plant named 'Yokingsville' as illustrated and described.

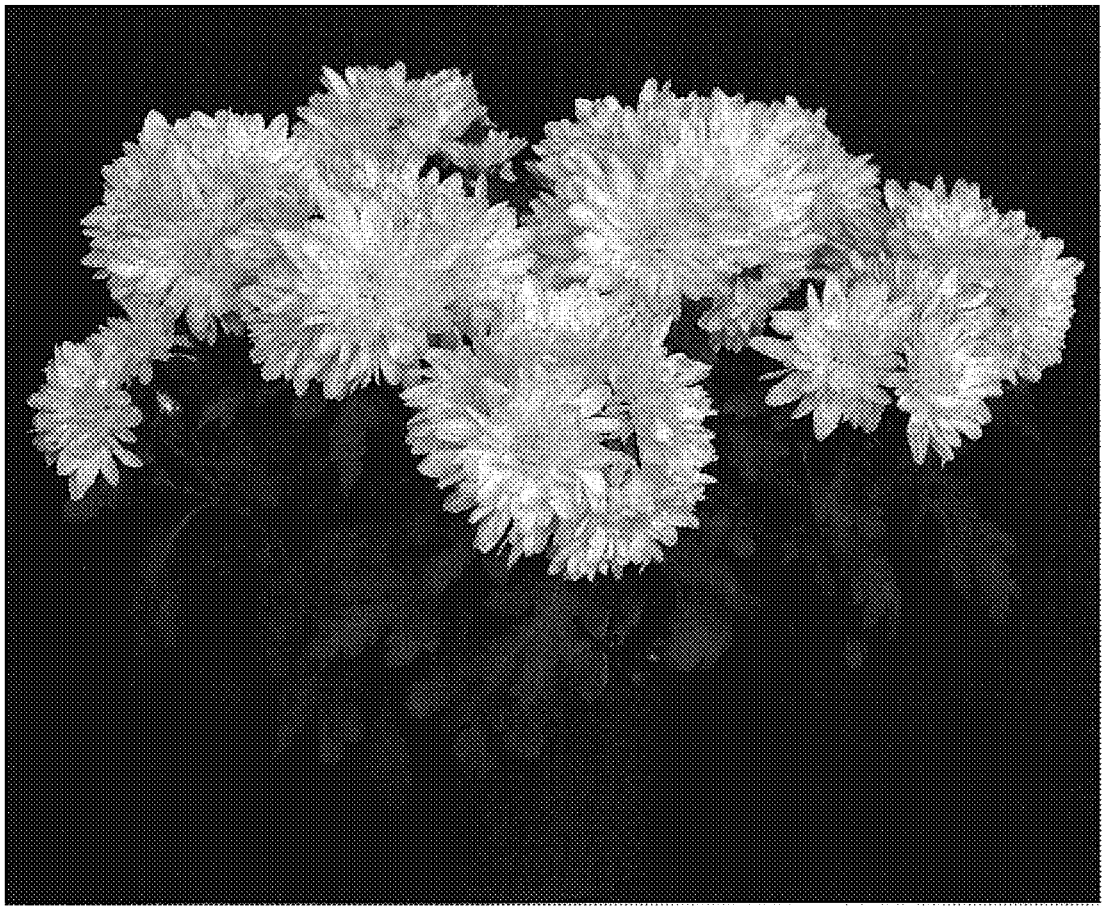

* * * * *